United States Patent [19]

Moreno

[11] Patent Number: 4,740,589
[45] Date of Patent: Apr. 26, 1988

[54] CAPSULAR POLYSACCHARIDE METAL COMPLEX VACCINES

[75] Inventor: Carlos Moreno, London, England

[73] Assignee: Burroughs Wellcome Co., Research Triangle Park, N.C.

[21] Appl. No.: 884,315

[22] Filed: Jul. 11, 1986

Related U.S. Application Data

[63] Continuation of Ser. No. 671,893, Nov. 15, 1984, abandoned.

[30] Foreign Application Priority Data

Nov. 23, 1983 [GB] United Kingdom ............... 8330968
Jun. 12, 1984 [GB] United Kingdom ............... 8414959

[51] Int. Cl.$^4$ .................. C07K 15/00; A61K 39/02
[52] U.S. Cl. ............................ 530/395; 530/350; 530/402; 530/403; 424/88; 424/92; 536/1.1; 536/123; 514/2; 514/6
[58] Field of Search ............... 424/92, 88; 530/350, 530/395, 402, 403; 536/1.1, 123; 514/2, 6

[56] References Cited

U.S. PATENT DOCUMENTS 4,384,113  5/1983  Daly ............................. 536/121
4,490,525  12/1984  Hayatsu et al. ............... 536/55.1

FOREIGN PATENT DOCUMENTS 0072513  2/1983  European Pat. Off.
0088303  9/1983  European Pat. Off.
0109688  5/1984  European Pat. Off.

OTHER PUBLICATIONS

Robuste et al., Cien & Ind. Farm 9, 1977, pp. 159–163, (English Translation).
Kedzierska, Chem. Abs., 67, 8845h, (1967).
Liu et al., Chem. Abs., 88, 168255t, (1978).
Zollinger et al., Chem. Abs., 96, 179171p, (1982).
Crescenzi et al., Chem. Abs., 94, 157409d, (1981).
Rendelman, Chems. Abs., 88, 165528h, (1978).
Rendelman, Chem. Abs., 89, 5477m, (1978).

*Primary Examiner*—Morton Foelak
*Assistant Examiner*—Garnette D. Draper
*Attorney, Agent, or Firm*—Donald Brown

[57] ABSTRACT

Complexes comprising a metal constituent and a bacterial capsular polysaccharide constituent, wherein the polysaccharide contains sialic acid, are useful in the prophylaxis and treatment of bacterial diseases. The polysaccharide is preferably colominic acid or meningococcal group B polysaccharide. Preferred metals are aluminum and ruthenium. The complexes preferably also contain a third constituent of bacterial outer-membrane protein. Some of the complexes, especially when formulated as vaccines, are particularly applicable in the prophylaxis and treatment of cerebrospinal meningits.

16 Claims, 6 Drawing Sheets

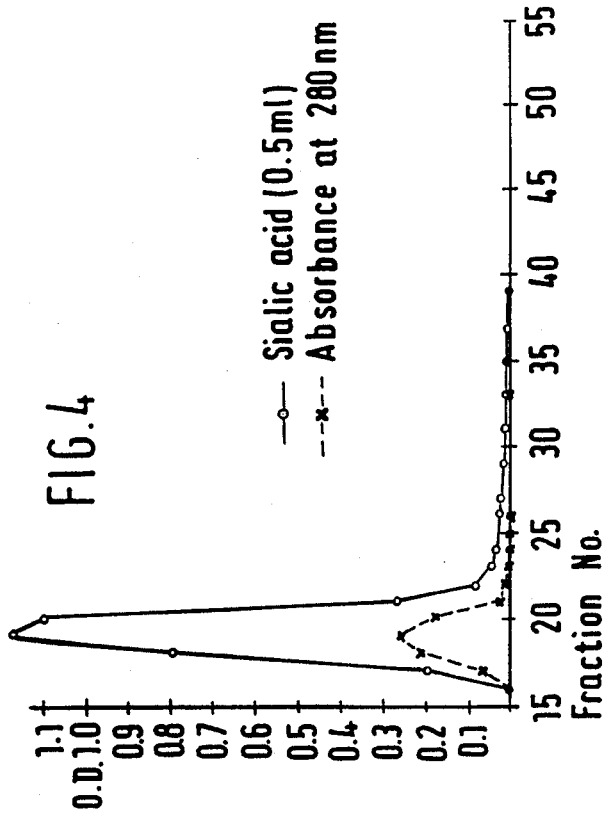
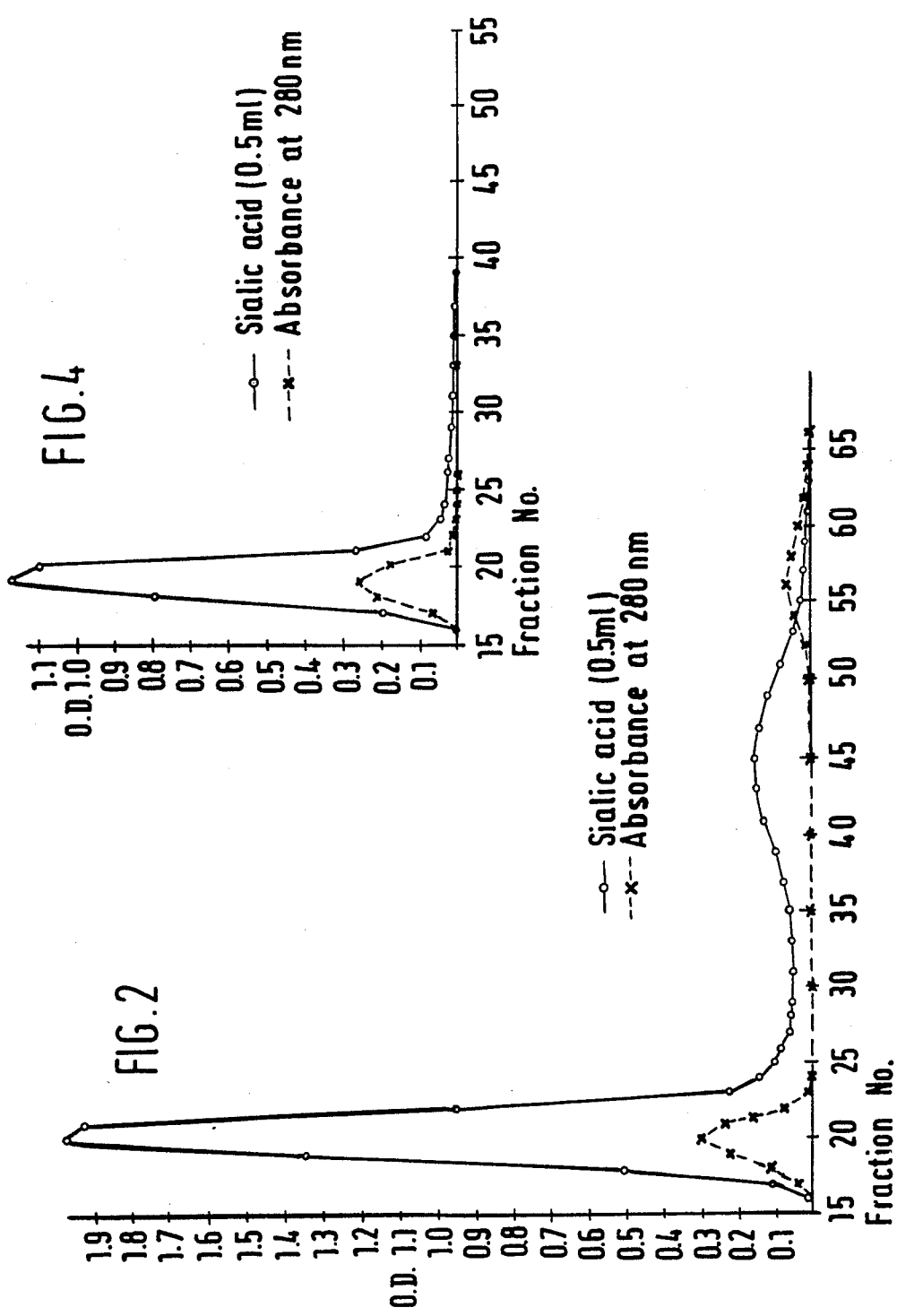

CAPSULAR POLYSACCHARIDE METAL COMPLEX VACCINES

This is a continuation of application Ser. No. 671,893, filed Nov. 15, 1984, now abandoned.

The present invention relates to novel complexes comprising polysaccharide and metal constituents and which are suitable for use in vaccines to provide protection against bacterial infections.

Certain bacteria, in addition to possessing an outer membrane structure which forms the boundary of cell envelope, also have an additional layer outside the membrane known as the capsule. An example of a gram negative bacterium with both of these features, is *Neisseria meningitidis (N. meningitidis)*. The outer membrane of the cell envelope, contains a number of substances, including lipopolysaccharides, pili (surface protrusions), major (high molecular weight) proteins, minor (low molecular weight) proteins, lipids, and lipoproteins. Of these, the first three have been identified as principal antigens. Another important class of antigens comprises the constituents of the capsule, known as capsular polysaccharides. Capsular polysaccharides and outer-membrane proteins are believed to exist as a non-covalent complex on the exterior of the bacterium. During growth, such bacteria continuously shed capsular polysaccharides and outer-membrane proteins, in their free and complexed forms. The polysaccharides, in both forms, can be precipitated from the culture by addition of a suitable electrolyte, which also precipitates most negatively charged polymers which are present.

The serology of *N. meningitidis* enables the associated capsular polysaccharide and outer-membrane proteins to be classified according to a recognized nomenclature. There are nine recognised serogroups A, B, C, L, X, Y, Z, W135 and 29E, further characterised into serotypes numbered 1-15 (see for example L.Weinstein and B. N. Fields (Eds), Seminars in Infectious Disease, Stratton Intercontinental Medical Book Corp, 1979 : Chapter 10; C. E. Frasch, Noncapsular Surface Antigens of *N. meningitidis*, pp. 308-310). Different strains within a group may possess the same serotype protein, and a number of ungroupable strains have also been discovered. The capsular polysaccharides are specific to particular serogroups (group specific polysaccharides) and the major outer membrane proteins are specific to particular serotypes (type specific proteins). However, the determinants of serotypes 4, 5 and 8 are lipopolysaccharides rather than outer-membrane proteins. Thus, the capsular polysaccharides may be referred to, merely by their serogroup specicifity (eg. Group B polysaccharide) and the outer membrane proteins by their serotype specificity, (e.g. type 2 protein). This convention is generally recognised, as referred to by: C. E. Frasch supra, C-M. Tsai et al in Journal of Bacteriology Vol. 146 (1981) pp.69-78, C. E. Frasch et al in Journal of Bacteriology, Vol 127 (1976) 973-981, N. A. Vendros in T. Bergan and J. R. Norris (Eds), Methods in Microbiology, Vol 10, Academic Press, London: Chapter XI, serology of the Meningococcus, or one of the following references : C. E. Frasch and S. S. Chapman, Infection and Immunity, Vol 6 (1972) pp. 674-681; J. T. Poolman, C.T.P. Hopman and H. C. Zanen, FEMS Microbiology Letters, Vol 3 (1982) pp. 339-348. For convenience, meningococcal capsular polysaccharides (MPS) of a particular serotype, say A or C, will be referred to by the abbreviation MPS (A), MPS (C) etc, and meningococcal outer-membrane proteins of a particular serotype say 2 or 6, will be referred to by the abbreviation T(2), T(6) etc.

The *Escherichia coli (E.coli)* strain conventionally designated K1, contains a capsular polysaccharide known as colominic acid. This is substantially identical in structure to MPS (B).

*N.meningitidis* normally inhabits the human nasopharynx and can cause the serious and often fatal disease, cerebrospinal meningitis to which infants are particularly vulnerable. *E.coli* K1 is also responsible for some cases of meningitis in the new-born. Previous attempts to identify and isolate meningococcal antigens, have concentrated on capsular polysaccharides and the principal outer-membrane antigens referred to above, namely lipopolysaccharides, pili and major proteins. The free capsular polysaccharides, MPS (A) and MPS (C) are reasonably successful in conferring immunity against meningococcal strains belonging to serogroups A and C respectively. Serogroup B has recently been identified with increasing infantile meningococcal infection and the lack of a vaccine effective against infection by group B meningococcal strains has created a growing demand for such a vaccine from international health authorities, eg the World Health Organisation. Some immunity to Group B strains may result from vaccination with MPS (A) or MPS (C) vaccines, but the protection provided is generally not sufficient in infants, and vaccines based on MPS (B) alone do not confer viable immunity against infection by group B strains.

Previously proposed vaccines based on free MPS(B) suffer from the additional disadvantage that they tend to be unstable. It is believed that this is because capsular polysaccharides which include sialic acid, for example MPS(B) and colominic acid, are prone to intra-molecular esterification between the polysaccharide residues (see R. Lifely, et al Carbohydrate Research, Vol 94 (1981) 193-203).

In UK patent application No. 8233317 there are described immunogenic, substantially pyrogen free compositions containing complexes of MPS(B) and certain outer membrane proteins which are less prone to the aforementioned instability of free MPS(B).

We have now discovered that the stability of polysaccharides which contain sialic acid, whether in the free form or in complex with bacterial outer-membrane protein, may be enhanced by complexing with a metal. It is known that some metals can complex with the capsular polysaccharides exuded by certain bacteria of the genera *Xanthomonas, Achromobacter* and *Pseudomonas* (for example *Xanthomonas fuscans*) when they inhabit the rhizosphere of plants. The pharmacokinetics of complexes of iron and non-bacterial polysaccharides (used for the treatment of anaemia) are described by Robuste et al in Cien. and Ind. Farm., 9 (1977) 159-63. Belgian patent specification No. 889 979 discloses a process for isolation of meningococcal and other capsular polysaccharide antigens wherein prior to separation of the polysaccharide per se it is extracted from culture as an intermediate complex with an organic quaternary ammonium salt in the presence of an inert porous support such as kieselguhr. The above references give no indication that sialic acid-containing polysaccharides may be stabilised by complexing with a metal.

Thus in one aspect the present invention provides a complex comprising a metal constituent and a bacterial capsular polysaccharide constituent, wherein the said bacterial capsular polysaccharide constituent contains sialic acid.

The sialic acid-containing bacterial capsular polysaccharide may for example be colominic acid or capsular polysaccharide specific to serogroup B of N. *meningitidis*.

Desirably, the said bacterial polysaccharide constituent is complexed with the said metal constituent and also complexed with a further constituent comprising bacterial (eg. meningococcal) outer-membrane protein. Such a complex of metal, polysaccharide and protein is hereinafter termed a triple complex.

The metal constituent may for example be selected from metals in groups IIA, IB, IIB and IIIB of the periodic table, as well as the transition metals, especially those of group VIII. Preferred metals include aluminium, ruthenium, zinc, iron, nickel and calcium. Other suitable metals may also include the folliwing in all of their various oxidation states: lithium, sodium, magnesium, potassium, scandium, titanium, vanadium, chromium, manganese, cobalt, copper, gallium, strontium, niobium, molybdenum, palladium, silver, indium, tin, tungsten, rhenium, platinum, gold and gadolinium. The metals are preferably provided in ionic form, (preferably derived from an appropriate metal compound) for example the $Al^{3+}$, $Ru^{3+}$, $Zn^{2+}$, $Fe^{3+}$, $Ni^{2+}$ and $Ca^{2+}$ ions. Especially preferred metals are aluminium and ruthenium, particularly in the form of the $Al^{3+}$ and $Ru^{3+}$ ions respectively. Such metals ions may be present in the complex alone or with other inorganic ions, eg-originating from metal salts from which the complex according to the invention is prepared (as further described hereinbelow). Thus for example, ruthenium ions may be present in the complex with one or more types of ion such as hydroxy, oxychloride and ammonium ions.

When present, the outer-membrane protein constituent may for example be selected from any of the proteins found in the outer-membrane of any strain of *N. meningitidis*, especially those specific to serotypes 1-3, 6, 7 and 9-15 and immunological equivalents thereof.

Outer-membrane proteins derived from mutants of *N. meningitidis* strains may be regarded as "immunologically equivalent" to those isolated from a particular meningococcal serotype when the gel electrophoresis characteristic patterns of the outer-membrane proteins of such mutants do not necessitate classification of the mutant organisms in another recognised serotype, and their immunological properties are not substantially altered. Such mutants may be found in nature as has been found with mutants of serotype 2 (per Poolman et al supra) or may be produced by techniques known to those skilled in the art.

Particularly preferred outer-membrane proteins are those specific to serotypes 6 and 2 of *N. meningtidis,* especially the serotype 2 protein having a single dominant component having a molecular weight of 42,000±3,000.

For convenience, references hereinafter to particular complexes or classes of complex according to the invention are referred to by an abbreviation of their constituents. For example, complexes lacking a protein constituent are termed metal-B, aluminium-B, aluminium-Col etc where 'B' refers to MPS(B) and 'Col' to colominic acid. Triple complexes according to the invention are termed for example metal-B2, aluminium-B6 etc where the number refers to the meningococcal serotype specificity of a particular polysaccharide constituent, and includes immunological equivalents as hereinbefore defined. The number '2' includes meningococcal serotype 2 protein having a single dominant component having a molecular weight of 42,000±3,000. Complexes of capsular polysaccharide and outer-membrane protein (which are starting materials in the preparation of certain complexes according to the present invention) are designated simply as B2, B6 etc.

A particularly preferred class of complexes according to the present invention are antigenic complexes, that is to say those complexes capable of raising antibodies in a mammal inoculated therewith. When intended for therapeutic use, such an antigenic complex may be provided in the form of an antigenic composition, substantially free from bacterial cells and from lipopolysaccharide, and wherein the metal constituent comprises a pharmacologically acceptable metal, preferably as an ion of the metal. Such a composition is substantially free from lipopolysaccharide in that it contains a weight percentage of lipopolysaccharide insufficient to produce significant toxic effects when a given amount of the composition is administered to the human or animal body. For normal administration doses of the composition, the weight percentage will be generally 1% or less. The lipopolysaccharide may be present in the free form or associated with another constituent of the composition, for example the polysaccharide protein complex.

The pharmacologically acceptable metal referred to above as a constituent of a complex contained in an antigenic compostion must be pharmacologically acceptable in the sense that its identity, chemical form (e.g. ion) and amount must be tolerated by the recipient for as long as it remains in the body thereof.

We have found that when experimental animals are immunised with an antigenic composition containing an antigenic triple complex according to the invention, antibody levels with respect to both serogroup-and serotype-specific antigens are increased, as compared with antibody levels achieved by immunisation with only a polysaccharide-protein complex. This contrasts with the well-known adjuvant effect of certain metal salts (including hydroxides), which would be expected to enhance antibody level only with respect to protein carriers such as serogroupspecific antigens. This observation provides evidence that the metal constituent of the triple complexes is actually complexed with the polysaccharide and protein constituents. We have also obtained an indication of complexing of metals with free capsular polysaccharides which contain sialic acid, by NMR and electrochemical measurements on an aluminium-Col complex, and by counter immuno-electrophoresis measurements of MPS(B) concentrations in solution as a function of time, with and without the presence of aluminium.

We have found that complexes according to the present invention usually have an apparent molecular weight of at least $2\times10^7$ when determined by chromatography on Sepharose CL-2B (Trade Mark). We have also observed that in complexes according to the invention which do not have a protein constituent, and wherein the metal constituent is aluminium, the ratio of sialic acid to aluminium is generally greater than 1:0.3 w/w.

Complexes according to the invention which have a protein constituent may be subjected to gel electrophoresis, particularly sodium docecyl sulphate-polyacrylamide gel electrophoresis (SDS-PAGE) to provide patterns characteristic of the components of the said protein constituent. For example, one may employ the SDS-PAGE procedure described by U. K. Laemmli in Nature (London) Vol 227 (1970) pp.680–685. The serotype specificity of meningococcal proteins in a complex according to the invention may for example be verified by comparison of its pattern with those given in the above literature references concerned with meningococcal serology and its experimental determination eg. C. E. Frasch et al in Journal of Bacteriology supra.

The serogroup specicifity of the capsular polysaccharide component of a complex according to the invention may be verified by any appropriate method of compositional analysis known to those skilled in the art. The sialic acid content of the polysaccharide consituent may be determined by colorimetric methods. The polysaccharide component may also be determined by nuclear magnetic resonance, or immunologically with specific antisera.

The antigenic compositions according to the present invention may optionally include one or more other antigenic components e.g. free MPS(A) and MPS(C) as well as one or more other complexes of meningococcal capsular polysaccharide and outer-membrane protein such as MPS(B)/T(7), MPS(C)/T(2) or MPS(A)/T(2) in order to provide a broader spectrum of immunity. The antigenic compositions may simultaneously contain more than one complex according to the present invention, for example aluminium-B2 and aluminium-B6.

In another aspect, the present invention also provides a process for preparing a complex according to the present invention, comprising bringing into association, bacterial capsular polysaccharide which contains sialic acid and, a metal.

Where the desired product is a triple complex, the capsular polysaccharide starting material may be provided in the form of a complex of the polysaccharide with bacterial (eg. meningococcal) outer-membrane protein, for example any of the proteins referred to above. The metal may for example be any of those indicated previously, and is generally employed as a compound thereof (eg as an ion of a metal salt). It is desirable that the metal and polysaccharide are brought into association in solution. This may entail admixture of a solution containing the polysaccharide and a solution containing the metal (eg. as a metal ion derived from a salt thereof), and optionally if desired, incubating the resulting mixture. Alternatively the two solutions may be brought into association by dialysis of one against the other. Preferably the solvent in each case is water, optionally containing one or more solubilising agents. Suitable metal salts include water soluble salts such as those derived from inorganic and organic acid anions, for example halides (ie. fluorides, chlorides, bromides and iodides) sulphites, sulphates, nitrites, nitrates, phosphates, alkanoates (eg acetates), fumarates, benzoates, succinates, phthalates and oxalates. When the metal is ruthenium, the salt conveniently may be "ruthenium red" that is ruthenium oxychloride, either in its normal or ammoniated form.

The polysaccharide or polysaccharide-protein complex used as a starting material in the process according to the invention, may be prepared by any method known to those skilled in the art, for example as described in the aforementioned references, or as disclosed in UK patent application No. 8233317. The latter application describes a process for the isolation of a complex of a bacterial capsular polysaccharide and a bacterial outer-membrane protein, the process comprising the steps:

(i) culturing in a medium, a bacterium which possesses an outer-membrane and capsule and obtaining an aqueous phase which includes a complex of a bacterial capsular polysaccharide and a bacterial outer-membrane protein;

(ii) admixing the aqueous phase obtained in step (i) with a quaternary ammonium salt, to effect precipitation of a precipitate containing the said complex;

(iii) admixing the precipitate obtained in step (ii) with a water-soluble salt of calcium or magnesium in an aqueous medium to form an aqueous solution which includes said complex as a solute;

(iv) admixing the aqueous solution obtained in step (iii) with a lower alkanol, to effect precipitation of a precipitate containing the said complex; and (v) separating the complex from any other components present in the precipitate resulting from step (iv).

The latter process provides the desired complex in a relatively pure form, substantially free, for example, from complexes other than that it is intended to isolate, lipopolysaccharides, lipids, nucleic acids and other impurities, and enable one to obtain the complexes directly.

In performing the latter process, the aqueous phase is desirably obtained before the culture has reached a stationary phase, in order to minimise the release of lipopolysaccharide. It is also advantageous to remove the bacterial cells and cell debris from the aqueous phase, for example by centrifugation, before performing the precipitation of step (ii), although such removal may be effected at any appropriate stage of the process. In step (ii), the quaternary ammonium salt is desirably cetyl-trimethylammonium bromide, ie Cetavlon (Trade Mark) or cetyl-pyridinium chloride. Such salts are used to form an insoluble complex salt with the free capsular polysaccharide which is present, and thus they are readily eliminated in steps (iii) and (iv). As well as the desired complex, the precipitate formed in this step of the process also contains most negatively charged polymers which are present in the aqueous phase, ie proteins (including those from the outer-membrane), lipopolysaccharide and partially degraded nucleic acids. When Cetavlon is used, the step (ii) precipitation is desirably performed at a temperature in the range from 12° to 25° C., optimally at or about 18° C. When the salt is cetylpyridinium chloride, the precipitation may be performed at a temperature in the range 0°–10° C., optimally at or about 4° C. In either case, the salt is preferably present at around 1% w/v.

The water-soluble salt referred to in step (iii) is preferably calcium chloride or aluminium chloride. As well as the complex, the solution in step (iii) also contains, as a solute, the other components present in the precipitate formed in step (ii), but not the capsular polysaccharide complex salt, which is thus eliminated.

In performing the latter process, the alkanol is used in step (iv) in an amount and at a concentration so that there occurs substantially no dissociation of any polysaccharide/protein complex present. Preferably, the alkanol is used to provide a concentration in the range of 50-95% v/v when in admixture with the aqueous solution. A particularly preferred concentration is about 75%. As used herein, the term "lower alkanol" denotes an alkanol containing 1 to 4 carbon atoms, for example ethanol or methanol. In addition to the complex, the precipitate formed in step (iv) also contains some low molecular weight impurities such as non-outer-membrane protein, low molecular weight nucleic acid fragments and a little lipopolysaccharide. These impurities are substantially eliminated in the separation in step (v), which is preferably performed by gel filtration, eg using Sepharose CL-2B or any other system having similar properties.

Further purification, if required, may be carried out on the product of step (v) in order to minimise the presence of contaminating materials such as degraded nucleic acids and uncomplexed polysaccharides and proteins.

The present invention further provides a vaccine formulation comprising an antigenic composition according to the present invention and at least one adjuvant and/or carrier therefor. In such formulations, the composition may include further antigenic components described above, such as one or more free meningococcal capsular polysaccharides. A vaccine intended to provide protection against meningococci of serogroups B and A and/or C can contain respectively a mixture of one or more complexes according to the invention, together with MPS (A) and/or MPS (C). Additionally or alternatively, such formulations may contain, if desired, complexes according to the invention, and one or more other complexes of meningococcal capsular polysaccharide and outer-membrane protein such as PMS(B)/T(7), MPS(C)/T(2) or MPS (A)/T(2), as well as more than one complex according to the present invention, for example aluminium-B2 and aluminium-B6.

The vaccine formulations according to the present invention may be presented in a sterile form, such as is suitable for administration to humans. In these formulations, the carrier may for example be water. Such a formulation may additionally or alternatively contain one or more appropriate non-metal constituents such as one or more metal salts (provided as adjuvants and not in the form of a complex), lactose as an antigen stabiliser, or one or more salts such as sodium chloride, to render the vaccine isotonic with blood. Preferably, an appropriate buffer is also included. In such vaccines, the complex according to the invention may conveniently be administered in a dosage of from 0.1 μg to 3 mg, desirably 1.0 to 300 μg, preferably about 50 μg.

The invention further provides a process for preparation of a vaccine formulation, the process comprising admixture of an antigenic composition according to the invention and at least one adjuvant or carrier therefor. In the process, the vaccine may be rendered sterile, eg. by detergent-assisted filtration.

In another aspect, the invention provides an antigenic complex according to the present invention for use in a method of prophylaxis or treatment of a bacterial (eg meningococcal or *E. coli*) disease of a mammal such as man. For example, the antigenic complex may be used for the prophylaxis or treatment of cerebrospinal meningitis. In such use, the antigenic complex may be presented in any formulation described herein. The antigenic complex may be administered in one or more doses. If more than one dose is administered, it is desirable that the administration is spaced over a suitable time scale to take advantage of secondary immunisation. The antigenic complex may for example be administered as two or three doses, for example over an interval one to three weeks. Where appropriate, doses subsequent to the first, may contain amounts of the antigenic complex which are less than the amount contained in the primary dose. The antigenic complex may be administered by any convenient route such as the parenteral (e.g. sub-cutaneous, intravenous, intra-peritoneal), oral, or as may be desirable for infants, intra-nasal route. The invention also provides a method of prophylaxis or treatment of a bacterial (eg meningococcal or *E. coli*) disease of a mammal such as man, comprising administration of an effective amount of antigenic complex according to the present invention to said mammal. The antigenic complex is advantageously employed in the form of an antigenic composition or a vaccine formulation according to the invention. The invention includes complexes produced by the process of the invention, as defined above.

BRIEF DESCRIPTION OF THE DRAWINGS

The following examples illustrate the present invention, reference being made to the accompanying drawings, in which:

FIG. 2 shows the elution profile of a typical crude B2 complex from a Sepharose CL-2B chromatographic column by monitoring absorbance of the fractions at 280 nm, and by sialic acid determination by the resorcinol-HCl colorimetric method.

FIG. 4 shows the elution profile upon Sepharose CL-2B re-chromatography of the purified typical B2 complex by monitoring absorbance of the eluent at 280 nm, and by sialic acid determination by the resorcinol-HCl colorimetric method.

EXAMPLE 1

ISOLATION AND PURIFICATION OF A B6 COMPLEX

Figure 1:
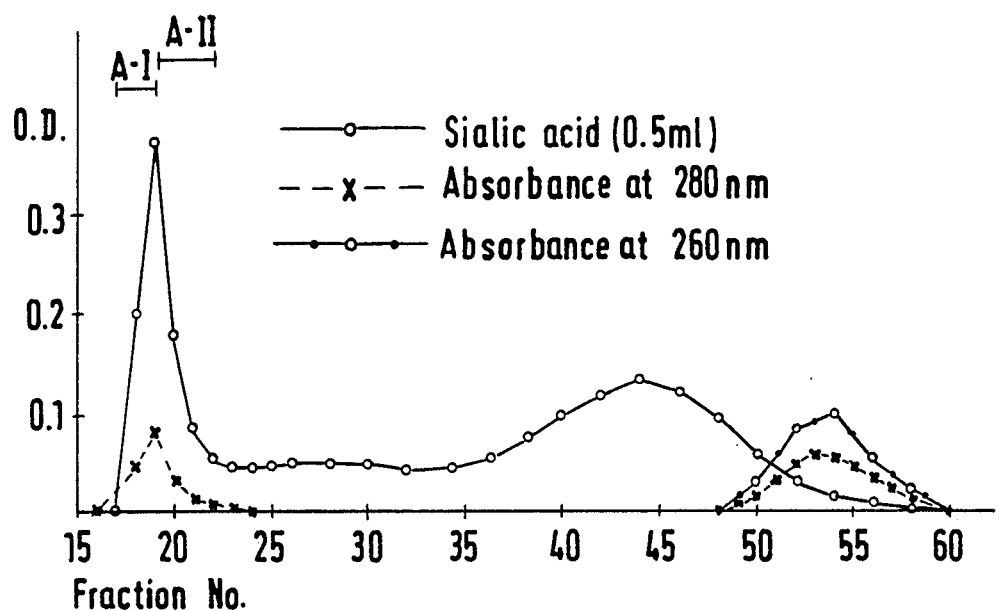
FIG. 1 shows the elution profile of a typical crude B6 complex from a Sepharose CL-2B chromatographic column by monitoring absorbance of the fractions at 260 and 280 nm, and by sialic acid determination by the resorcinol-HCl colorimetric method.
Figure 3:
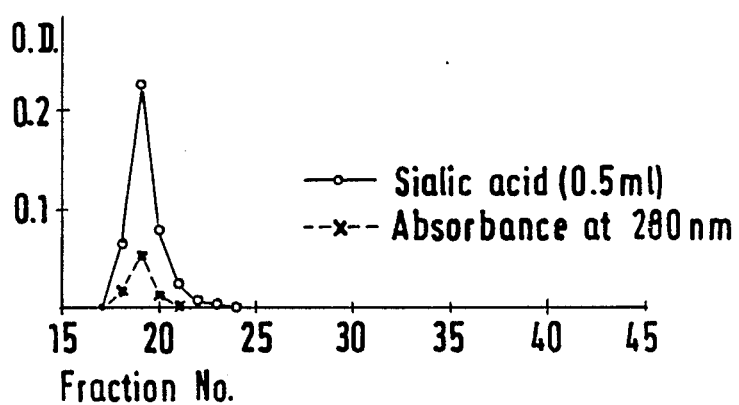
FIG. 3 shows the elution profile upon Sepharose CL-2B re-chromatography of the purified typical B6 complex by monitoring absorbance of the eluent at 280 nm, and by sialic acid determination by the resorcinol-HCl colorimetric method.
Figure 5:
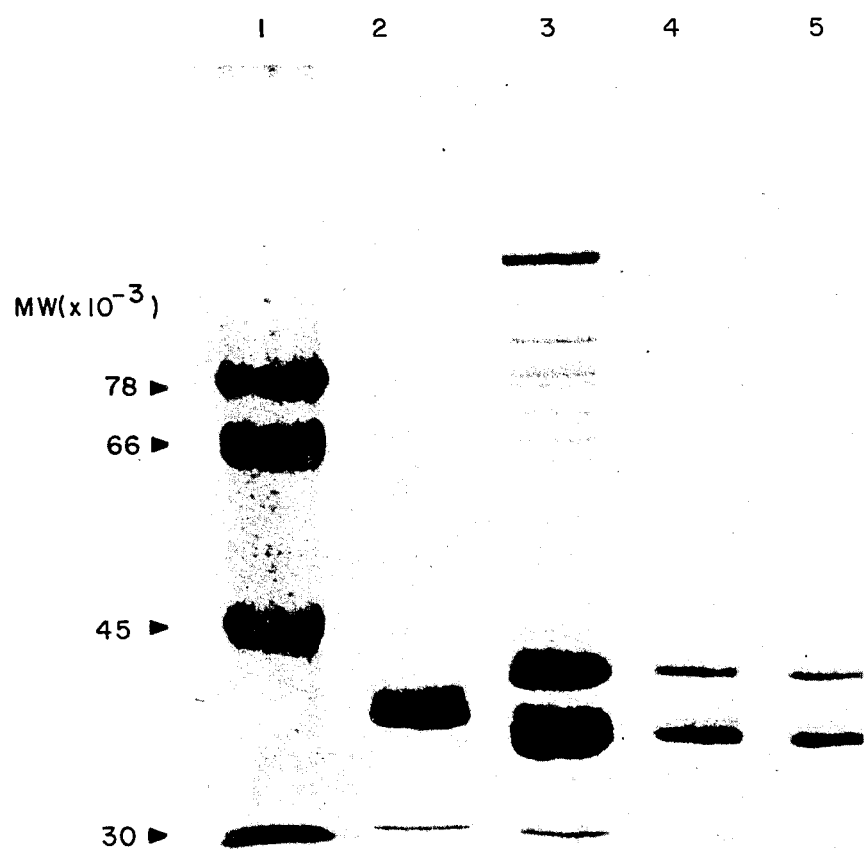
FIG. 5 shows patterns obtained from SDS-PAGE of B2 and B6 complexes, and molecular weight marker standards.
Figure 6:
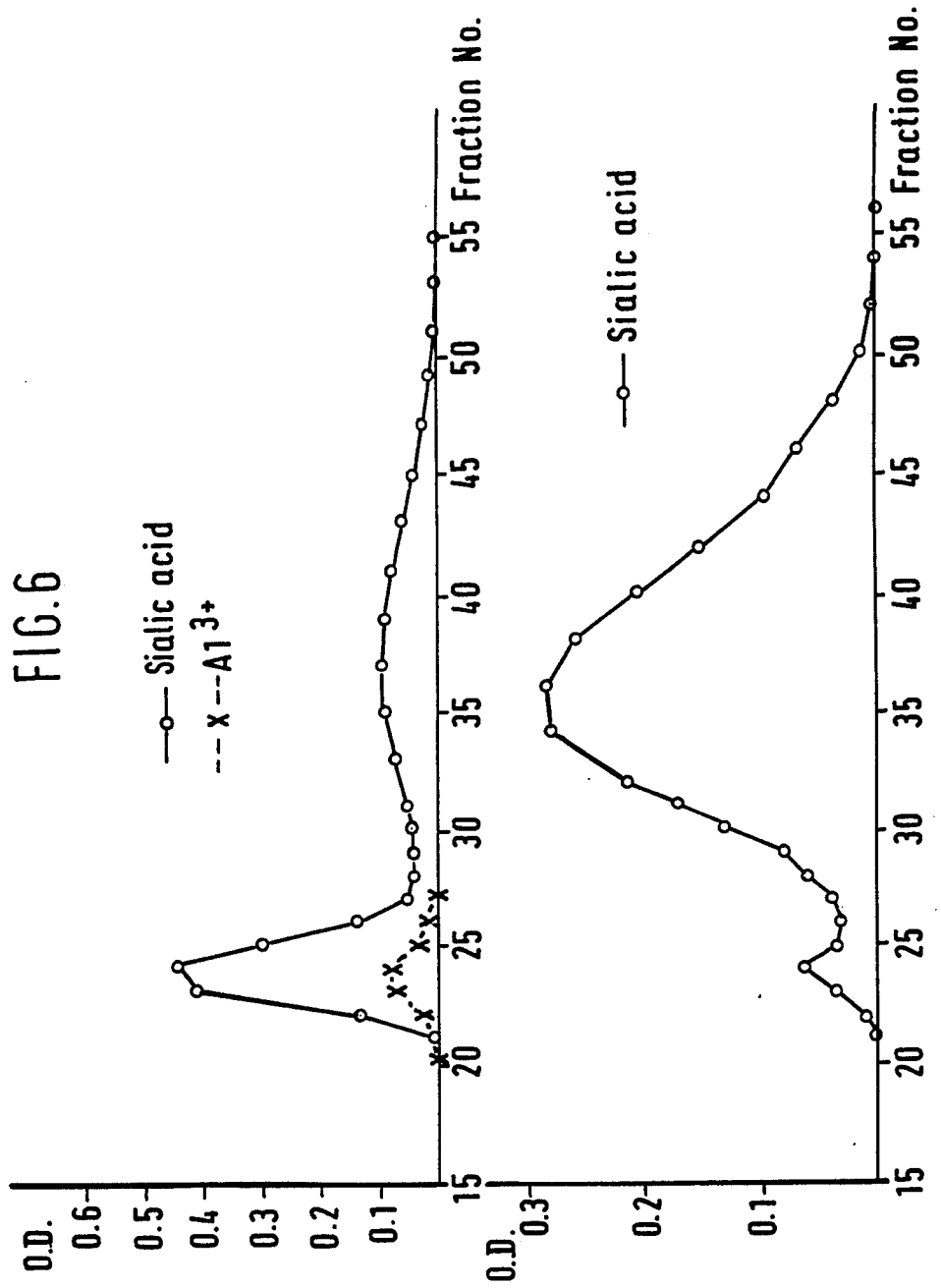
FIG. 6 shows the elution profile upon Sepharoso CL-2B rechromatography of an aluminium B-complex and pure MPS(B) as monitored for aluminium and sialic acid.

A culture medium was prepared as an aqueous solution of the following ingredients, in the amounts stated, and the resultant solution was made up to a volume of 16 litres with added water.

|  | per 16 liters |
|---|---|
| $K_2HPO_4$ | 3.68 g |
| L-Glutamic acid | 20.8 g |
| Cysteine HCl | 0.48 g |
| $NaHCO_3$ | 13.47 g |

-continued

|  | per 16 liters |
|---|---|
| Tricine, N tris (hydroxymethyl) methyl glycine | 11.46 g |
| $FeSO_4 7H_2O$ | 0.045 g |
| $NH_4Cl$ | 8.0 g |
| $K_2SO_4$ | 0.77 g |
| $CaCl_2 2H_2O$ solution, 7.4 mg/100 ml | 16 ml |
| $MgCl_2 6H_2O$ | 1.71 g |
| Casein Hydrolysate | 320 g |

The pH of the solution was adjusted to pH 7.2 and two 400 ml aliquots were transferred to two, one litre conical flasks. The remainder of the solution was transferred to a 15 litre bottle. A siphon was connected to the bottle and both flasks and the bottle were autoclaved for 15 minutes at a pressure of 15 lb/sq inch. The contents of the bottle were then transferred to a 20 litre ferm enter and 300 ml of sterile 50% aqueous glucose was added, to form the medium. An inoculum was prepared by adding one drop of a culture containing a serogroup B, serotype 6 strain of *N. meningitidis*, to both flasks containing 400 ml of the solution.

The flasks were incubated at 37° C., with shaking, for 12 hours, to form 800 ml of seed culture, the purity of which was checked by the Grams stain technique.

All of the seed culture was then used to inoculate the medium in the fermenter. The whole culture medium was then grown under the following experimental conditions.

| Temperature constant at 37° C. | |
|---|---|
| pH | constant at 7.2 with sterile $2\underline{N}$ HCl and $2\underline{N}$ NaOH |
| Stirring speed | 100–700 rpm automatically adjusted. |
| Dissolved oxygen | minimum 10% saturation. |
| Air flow | 1–5 liter per minute adjusted manually to maintain dissolved oxygen concentration. |
| Antifoam | Polypropylene glycol added manually when required. |

The culture was allowed to grow until an optical density of approximately 9.0 was reached. This O.D. might normally be expected to be achieved after about 6.5 hours.

The culture was then transferred from the fermenter and passed through a continuous flow centrifuge at a flow rate sufficient to produce a substantially clear supernatant. Following the centrifugation, to the supernatant was added, 10% by volume of 10% w/v Cetavlon in water, to produce a precipitate in suspension. The suspension was centrifuged at 2000 rpm at 4° C. The supernatant was then discarded, and the precipitate was suspended in 600 ml of water. 600 ml of 2M aqueous calcium chloride was then added and the mixture stirred for 1 hour at 4° C., then centrifuged for 20 minutes at 5000 rpm.

To the supernatant was added one drop of caprylic alcohol as an anti-foaming agent and the supernatant was de-gassed under vacuum, with stirring, for 10 minutes. The de-gassed supernatant was stood in an ice bath, and to it was added 3 volumes of absolute ethanol at 0° C. with continuous stirring. The mixture was then stood in the bath for two hours before being centrifuged at 5000 rpm for 15 minutes, at a temperature of 4° C. The supernatant was discarded and the precipitate re-suspended in 75% ethanol and centrifuged to form a pellet which may be stored at −20° C. or treated as below.

The pellet was suspended at a rate of 20 mg/ml in 0.1M ammonium acetate containing 0.01% thiomersalate. The suspension was subjected to ultrasonic agitation for 10 minutes, and passed through a 3 μm membrane to remove insoluble material. The supernatant was then passed through a 5 litre column of Sepharose CL-2B equilibrated with buffer at 4° C. The column was washed through with buffer, and the effluent monitored by UV absorption at the wavelength 260 and 280 nm and resorcinol-HCl sialic acid determination. The void volume fractions exhibiting absorption at 280 nm and containing sialic acid (resorcinol-HCl determination) were pooled. Sodium deoxycholate was added up to a final concentration of 0.1% w/v buffered to within pH 8–9. (Other concentrations and pH values are also possible, eg a final concentration of 1% w/v buffered to pH 11 has been found to reduce the amount of material which adheres to the membrane). The resultant solution was immediately filtered through a Sartobran 0.22 capsule with a 0.45 prefilter. The filtrate was precipitated with 3 volumes of absolute ethanol (concentration after solution about 75%). After this filtration, all procedures were performed under sterile conditions. After centrifugation, the supernatant was then discarded, and the precipitate suspended in 200 ml of cold ethanol to wash it. The suspension was then centrifuged, the supernatent discarded, and the precipitate (which comprised substantially only the B6 complex) was, again subjected to the same washing process before being redissolved in 200 ml of cold water. (Alternatively, injectable solutions may be prepared eg. with 5% lactose and 0.01 M $Na_3 PO_4$; pH 7.3).

EXAMPLE 2

ISOLATION AND PURIFICATION OF A B2 COMPLEX

A B2 complex was prepared by the process of Example 1, starting from a culture containing a serogroup B, serotype 2 strain of *N. meningitidis*.

EXAMPLE 3

Isolation and Purification of a B6 Complex: Small-Scale Process

Three litres of diluted culture medium were prepared by a method analogous to that used in Example 1, using the same ingredients. A portion of about 200–500 ml of the medium was transferred to a non-baffled shaped-flask and inoculated with 1 drop of a culture containing a serogroup B, serotype 6 strain of *N. meningitidis*. The inoculum was incubated as specified in Example 1, then added to the remainder of the culture medium, which was incubated in a manner analogous to that described in Example 1, for 6.75 hours. The culture was then transferred as 6×500 ml to a centrifuge and centrifuged for 20 minutes at 7000 rpm.

To the supernatant was added 10% by volume of 10% w/v Cetavlon. The suspension was left to settle at 4° C. for 16 hours, after which, the major part of the supernatant was syphoned off, and the remainder, containing the precipitate, was centrifuged at 2000 rpm for 20 minutes at 4° C. The precipitate was resuspended in 20 ml of distilled water, 20 ml of 2M $CaCl_2$ was added, and the mixture stirred for 1 hour at 4° C., then centrifuged for 20 minutes at 5000 rpm.

The crude precipitate was redissolved and part-purified by chromatography on a 500 ml column of Sepharose CL-2B, as described in Example 1. The void volume fractions containing sialic acid and material absorbing at 280 nm were pooled, precipitated by addition of ethanol to a final volume of 75% v/v, then collected by centrifugation at 15,000 g for 20 minutes at 4° C. The precipitate was washed with absolute ethanol and freeze-dried in 5% lactose and 0.01M $Na_3PO_4$; pH 7.3.

EXAMPLE 4

ISOLATION AND PURIFICATION OF A B2 COMPLEX: SMALL SCALE PROCESS

A B2 complex was prepared by the process of example 3, starting from a culture containing a serogroup B, serotype 2 strain of *N. meningitidis*.

EXAMPLE 5

Characterisation of B2 and B6 Complexes

The complexes formed in Examples 1-4 were identified in each case as the peak eluting in the void volume on Sepharose CL-2B (MW $20\times10^6$) at 4° C. as assayed for sialic acid by the resorcinol-HCl method and for absorbance at 260 and 280 nm in the case of B6 complexes (see FIG. 1) and at 280 nm only in the case of B2 complexes (see FIG. 2). The latter plot was obtained from a freeze-dried sample of a B2 complex having a sialic acid content of 48% and a protein content of 36.1% (ratio 1.33:1). The complexes were found not to dissociate (ie. protein and polysaccharide remain in the void volume) upon re-chromatography on Sephrose CL-2B (FIG. 3 for the complex used in FIG. 1 and FIG. 4 for the complex used in FIG. 2) at 4° C. SDS-PAGE of the complexes gave the protein component pattern characteristic of serotype 6 for the products of Examples 1 and 3 and serotype 2 for the products of Examples 2 and 4; the samples were boiled for 3 minutes in SDS at 95° C. then subjected to the procedure of Laemmli supra. 10 μg of sample per track, staining with Coomassie blue. In FIG. 5, track 1 shows molecular weight marker bands. Track 2 was obtained from a B2 complex. The pattern of track 2 shows a major band due to a dominant protein component having a molecular weight in the region of 42,000. A minor band also appears around 32,000. Track 3 was obtained from a crude precipitate including B6 complex obtained by precipitation with 1% Cetavlon and before purification) Tracks 4 and 5 were obtained from samples of freeze-dried B6 vaccine compositions obtained from isolation processes including precipitation with cetylpyridinium chloride, the tracks being from samples, respectively before and after sterile filtration. In both tracks 4 and 5, the two bands have apparent molecular weights of around 38,000 and 43,000. Chemical composition of the complexes was determined by colorimetric methods, for sialic acid (resorcinol-HCl), and for protein (Lowry method using a standard of bovine serum albumin).

EXAMPLE 6

Preparation of an Aluminium-B-6 Complex (i) A B6 complex, isolated by the method of Example 1 was complexed with aluminium by preparation of a solution as 0.5 ml aliquots, each containing: b 100 μg B6 complex in 5% lactose; 0.01M sodium phosphate to pH 7.4; 0.001M $Al_2(SO_4)_3$.

(ii) A B6 complex, isolated by the method of Example 1 was complexed with aluminium by preparation of an aqueous solution of the B6 complex (3 ml) at 0° C., to which was added $2\times10^{-2}$M $AlCl_3$ to give a molar ratio of sialic acid: aluminium of between 1:0.1 and 1:3. Following incubation for 10 min. at 0° C., the solution was made to 0.1M w.r.t. NaCl and 3 volumes of absolute ethanol were added. The precipitate was collected by centrifugation, suspended in absolute ethanol and recentrifuged, and finally redissolved or resuspended in water (3 ml). An equal volume of 0.02M $Na_3PO_4$ pH 7.3 and 10% lactose buffer was added, and aliquots were freeze dried.

EXAMPLE 7

PREPARATION OF A RUTHENIUM-B6 COMPLEX

In a manner analogous to that described in Example 6, the title complex was prepared using 100 μg of B6 complex in 5% lactose; 0.01M sodium phosphate to pH 7.2; 0.001M ruthenium red (ammoniated ruthenium oxychloride).

EXAMPLE 8

ISOLATION AND PURIFICATION OF MPS(B)

Three 15 litre tanks of diluted culture medium, were prepared by a method analogous to that used in Example 1, using the same ingredients. Each tank was seeded with 800 ml of fresh medium, the seed being prepared from a culture (containing a serogroup B strain of *Neisseria meningitidis.* The tanks of medium were incubated in a manner analogous to that described in Example 1, for about 5.5 hours, and harvested into 15 litre bottles. The contents of these bottles was then spun-down by centrifuging at 40–50,000 rpm, the speed varying according to the density of the harvest. Immediately after harvest, 150 ml of 10% Cetavlon was added to each partially-clarified batch of supernatent, which was then left at 4° C. to settle.

After two days, most of the supernatent was syphoned off from the 15 litre bottles and the remainder was combined and spun down in 4 one-litre portions.

The spun-down precipitates were stored at minus 20° C., and were later suspended in 300 ml of 1/10 saturated sodium acetate, pH 7.0. 300 ml of 2M $CaCl_2$ was added to the suspension, and the mixture was stored for 1 hour at 4° C. Absolute ethanol was then added to form a concentration of 25% v/v, the total volume added being 200 ml. The precipitate was spun-down and the supernatent retained. The supernatent was filtered through a No. 50 filter paper to clarify it. The thus filtered supernatent was perfectly clear to the eye.

The ethanol concentration in the supernatent was then increased to 75% v/v by the addition of a further 1600 ml of absolute ethanol.

The precipitate was then spun-down in 4 one litre portions. The supernatent was discarded and the precipitate washed twice in ethanol and twice in acetone. The wet weight yield was 2.5 g. After storage at −20° C., the precipitate was dissolved in 350 ml of 1/10 saturated neutral sodium acetate, to yield an opalescent solution.

The precipitate solution was thawed and extracted twice with two 0.5 volumes of cold phenol (100 g crystalline phenol plus 40 ml 1/10 saturated neutral sodium acetate). The extraction was achieved by shaking in the hand for approximately 1 minute. Phase separation was effected by centrifugation at 7,000 rpm (9,400G) in polypropylene pots. During this process, the temperature was raised to 10° C., to give better phase separation. The phenol phase was discarded, and the aqueous phase was extracted with chloroform/butanol 5:1 by homogenisation. Phase separation was achieved as above, but using glass pots with spinning at 580 rpm (4,800G) for 30 minutes. The aqueous solution was removed and stored at −20° C.

The slightly opalescent material obtained above, was thawed and dialysed for 18 hours agains 0.1M $CaCl_2$ (5 litres). The volume after dialysis was 250 ml. This was distributed amongst 50 ml centrifuge tubes and spun for 3 hours at 100,000G. The clear supernatent was poured-off of the gelatenous precepitate produced (which was discarded).

750 ml of absolute ethanol was added to precipitate the meningococcal group B polysaccharide after 1 hour to allow for complete precipitation. The polysaccharide precipitate was washed twice with ethanol and twice with acetone and then dried. The dry weight yield was 0.983.

EXAMPLE 9

ISOLATION AN D PURIFICATION OF MPS(B); SMALL-SCALE PROCESS

The methodology of Examples 1–4 and 8 was followed, using a seed from a culture of serogroup B *Neisseria meningitidis* with a culture time of 6.5 hours, to produce 1800 ml of culture which was spun-down to yield slightly cloudy supernatent. 18 ml of 10% Cetavlon was added and left overnight at 4° C. The precipitate thus formed, was spun-down and resuspended in approximately 100 ml if distilled water and stored at −20° C. Further addition of Cetavlon to the consequent supernatent did not produce any further precipitation. The Cetavlon precipitate was dissociated with 100 ml of 2M $CaCl_2$ (stirred at 4° C. for 1 hour).

A second batch of culture was similarly prepared, using a culture time of 6.25 hours. Most of the harvest was extracted and spun-down as before, to yield 1500 ml of supernatent. This was concentrated by ultrafiltration, choosing a 100,000 MW cutoff. Final volume was approximately 150 ml and the filter was back-washed to produce final volume of 162 ml. This opalescent liquid was spun down at 8,000G to achieve clarification. 0.9 ml was taken and 0.1 ml of 10% Cetavlon was added. Precipitation was immediate. A further 1.2 ml was taken and 0.4 ml of absolute ethanol was added, to achieve a total ethanol concentration of 25% v/v. There was no increase in precipitation and a further 3.2 ml of absolute ethanol was added to 75% v/v, which produced only a very slight cloudiness.

The culture was spun-down as for the first batch. 1500 ml of opalescent supernatent were stored overnight at 4° C. and then diafiltered using as 100,000 MW cut-off membrane to produce 162 ml of retentate. This material was spun-down at 8,000G to clarify, the pellets being retained. A precipitate was obtained from the resultant liquid by addition of 0.1% Cetavlon. 1.2 ml of supernatent taken and 0.4 ml of absolute ethanol were added to 25% v/v. No precipitation occured, indicating very little lysed proteinaceous material in the culture. Increase in the ethanol concentration to 75% v/v, by addition of 3.2 ml of absolute ethanol, produced only slight cloudiness, indicating either much release of polysaccharide below 100,000 MW or low polysaccharide yield.

The first possibility was checked by adding Cetavlon to the dialysate from the ultrafiltration apparatus. No precipitation occured, indicating the second of the options above. The remainder of the retentate (159.8 ml) was further concentrated overnight by vacuum dialysis to 44 ml, 1 ml of which was removed. The concentrate was readily precipitated with 0.1% Cetavlon. The remaining 42 ml was precipitated by addition of 126 ml of absolute ethanol to 75% v/v (no discernable precipitation occuring at 25%). The precipitate increased on standing, but no observable increase was produced by addition of 1.26 g of ammonium acetate. The precipitate gradually aglommerated.

The pH of the solution was found to be 7.4. The total quantity of precipitate obtained, was washed twice with ethanol and twice with acetone, then dried; the dry weight yield was 40 mg.

EXAMPLE 10

PREPARATION OF AN ALUMINIUM-B COMPLEX (DIALYSIS METHOD)

Meningococcal group B polysaccharide (20 μmol sialic acid) was dialysed against $AlCl_3$ solution (20 μmol $Al^{3+}$ in two litres of distilled water) at 4° C. for 24 hours. The solution inside the dialysis sac, was precipitated with 75% v/v EtOH, the precipitate centrifuged, and the pellet freeze-dried. Analysis of the B polysaccharide-aluminium complex for sialic acid, $Ca^{2+}$ and $Al^{3+}$ ions gave a molar ratio of 1.00:0.01:0.34. Analysis of metal ions was afforded by atomic absorption spectroscopy.

EXAMPLE 11

PREPARATION OF AN ALUMINIUM-B (INCUBATION METHOD)

Group B Polysaccharide (20 μmol sialic acid) was incubated with $AlCl_3$ (2–20 μmol $Al^{3+}$) in distilled water (2 ml) at room temperture for 10 minutes. 1M ammonium acetate (0.2 ml) was added, and the solution precipitated with 75% v/v EtOH. The precipitate was centrifuged, and the pellets freeze-dried. At the higher $Al^{3+}$ molar ratios (i.e. sialic acid: $Al^{3+}$ 1:1 and 1:0.5) a water-insoluble complex was obtained, whereas at lower $Al^{3+}$ molar ratios (i.e. sialic acid: $Al^{3+}$ 1:0.3, 1:0.2 and 1:0.1) the complex was water-soluble.

EXAMPLE 12

CHARACTERISATION OF ALUMINIUM-B COMPLEXES

The molecular weight of the metal complexes formed by the methods of Examples 10 and 11 was investigated by Sepharosae CL-4B Chromatography. In both cases, the void volume peak ($V_o$) contained sialic acid and aluminium. The complex obtained from the method of the latter example, however, had an increased molecular weight (see FIG. 6).

EXAMPLE 13

IN-SITU PREPARATION OF ALUMINIUM-COL AND ALUMINIUM-B COMPLEXES AND THEIR CHARACTERISATION

NMR and electrochemical measurements on aluminium-colominic acid systems were performed to provide characterisation data and evidence of complex formation. Counter immuno-electrophoresis measurements of time-dependant degradation of MPS(B) in solution, with and without the presence of aluminium, were also used. In each of these experiments, the polysaccharide and aluminium are brought into association during preparation of the various experimental test solutions. The corresponding complexes were thus formed in situ.

Figure 7:
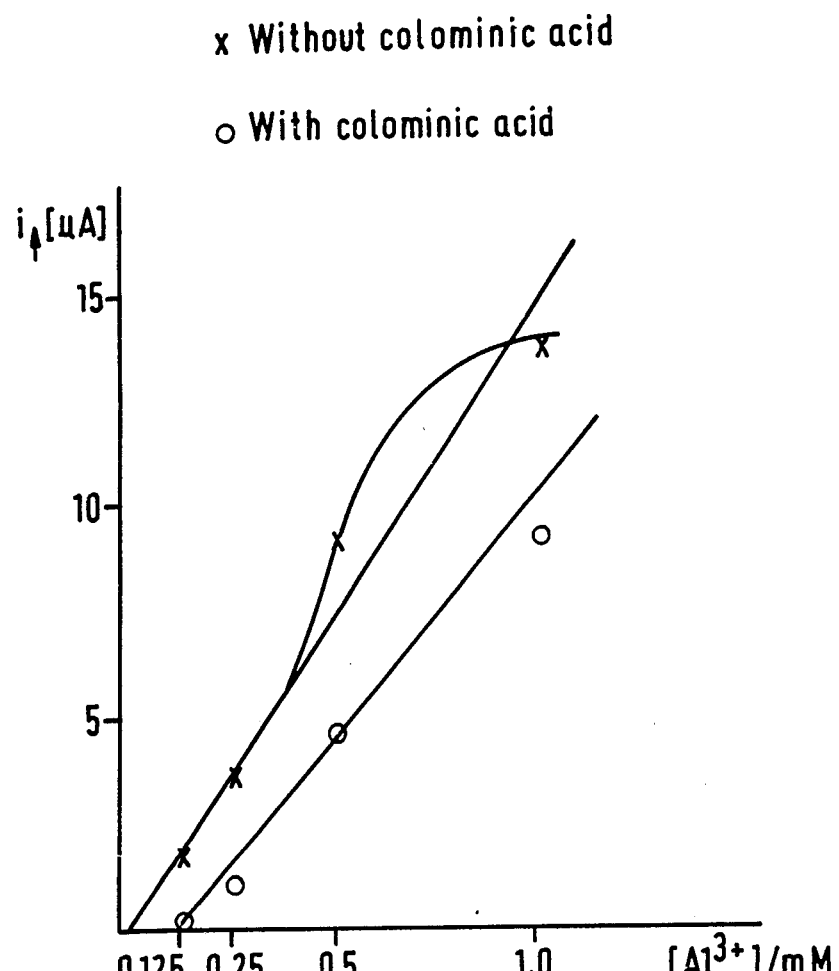
FIG. 7 shows a polarographic DPP plot of peak current as a function at $Al^{3+}$ concentration in solution, with and without the presence of colominic acid.

(a) Electrochemical measurements Two (0.125 mM to 1 mM) $Al^{III}$ concentration series were polarographed, one in the absence of the polysaccharide, and the other in its presence at constant concentration 1 mM wrt. The monomer (NANA) or 10 $\mu$M (8–16 $\mu$M) wrt. the polymer. As indicated by the DPP plot show in FIG. 7, =10 mM colominic acid in 0.137 M-NaClO$_4$ were found to bind on the order of 100 $\mu$M-Al so that up to this aluminium concentration, no free metal ions are found to be present in the mixture. Since the colominic acid dilution data are somewhat divergent with respect to the free Al data, secondary binding of aluminium is suggested, the extent of which is given by the difference of the slopes (derivatives) of the two curves.

In the unbuffered solutions, pH was controlled by hydrolysis of aluminium and by proton transfer equilibria of colominic acid. Whilst the pH of the background solution was 8.721, aluminium sulphate at 1 mM reduced the pH to 4.191. The pH then increased with dilution exponentially to 4.857 at 125 nM-Al$_2$ (SO$_4$)$_3$. Colominic acid gave pH 6.739 at 1 mM (wrt. NANA), which increased very little with dilution, to 6.784 at 125 nM (wrt. NANA). Equimolar mixture of 1 mM each (polysaccharide (wrt. NANA) plus aluminium III) gave pH 3.927. This suggests that increased proton dissociation by colominic acid results from aluminium binding (e.g. release of hydroxylic protons to form metal-oxygen bonds) or that the acidification of the unbuffered mixture results from hydrolysis of aluminium as a result of binding the minority species of the aluminium.

(b) NMR measurements $^{13}$C n.m.r. showed that Al-(III) complexed primarily at the carboxylate group but that other interactions were present and that several slowly exchanging species were present in aqueous solutions.

(c) Counter immunoelectrophoresis measurements

Figure 8:
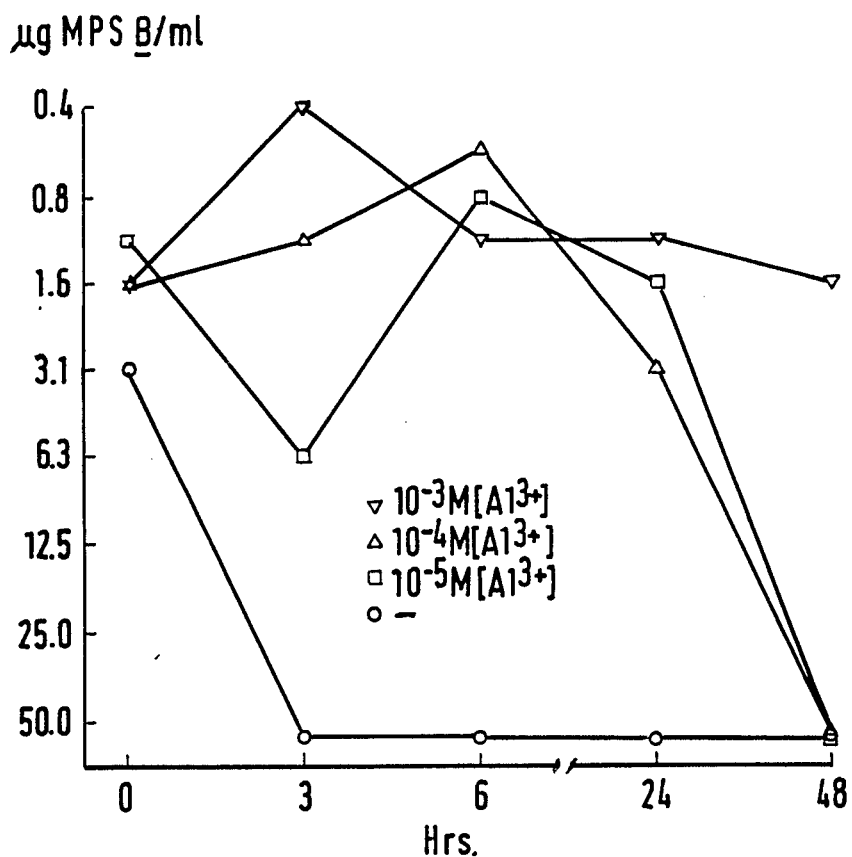
FIG. 8 shows counter immuno-electrophoresis measurement of the time-dependent degradation of MPS(B) in solution, with and without various concentrations of $Al^{3+}$.

The persistence in solution of MPS(B) as a function of time, with and without the presence of $Al^{3+}$ ($10^{-3}$, $10^{-4}$ and $10^{-5}$M) was monitored by counter immunoelectrophoresis (pH 4.0 antiserum: Rabbit $\bar{a}$ Meningo B ES.77.1). Results are shown in FIG. 8. The stabilisation of MPS(B) observed is the presence of $Al^{3+}$ is evidence of complexing of the metal ion with the sialic acid repeat unit.

EXAMPLE A IMMUNISATION OF MICE WITH METAL-B6 COMPLEXES (a) Aluminium-B6

The level of antibodies produced against group B and type 6 meningococcal antigens respectively, was measured in mice at 7 days after secondary immunisation with an aluminium B6 complex prepared by the method of Example 6. Mice were injected intaperitioneally with the test and reference preparations indicated below.

Individual bleedings were taken from the mice at 7 days after immunisation. The antibody level was detemined as $\mu$g/ml of serum, by solid phase radioimmunoassay in plate sensitised with purified group B meningococcal polysaccharide. In this method, microtiter soft plates were pre-treated with poly L-lysine (Sigma, 100 $\mu$g per ml) and sensitised with the polysaccharide. After incubation with the complex, wells were counted and a linear correlation between the counts and log$_2$ of the serum dilution was obtained. Extrapolated values at 1/50 dilution of serum were compared with linear correlations of a standard.

Test and reference preparations in each case were prepared as follows:

| Preparation No. | Injection Solution |
|---|---|
| 1. | 10 $\mu$g B6 complex, 5% lactose, 0.01 M Na$_3$PO$_4$ pH 7.4 (0.5 ml) i.p. |
| 2. | 5% lactose, 0.01 M Na$_3$PO$_4$ pH 7.4 (0.5 ml) i.p. |
| 3. | Solution of Example 6 (0.5 ml) i.p. |
| 4. | 5% lactose, 0.01 M Na$_3$PO$_4$ pH 7.4, 0.001 M Al$_2$(SO$_4$)$_3$(0.5 ml) i.p. |

The antibody responses to each preparation for group B antigens are shown in the following Table.

ANTIBODY RESPONSES FOLLOWING IMMUNISATION OF CBA MICE

| Preparation No. | Anti-B Response $\mu$g/ml antibody in serum (standard error) |
|---|---|
| 1. | 1.6 (1.38) |
| 2. | 0.49 (1.04) |
| 3. | 3.92 (1.16) |
| 4. | 0.65 (1.20) |

(b) Ruthenium-B6

The complex produced in Example 7 above was tested in an analogous manner to that described above, in female CBA mice, 5 per group. Individual bleedings were taken 7 days after immunisation and anti-B antibody serum levels determined by solid phase radioimmunoassay.

Test and reference preparations in each case were prepared as follows:

| Preparation No. | Injection Solution |
|---|---|
| 1 | 10 $\mu$g B6 complex, 5% lactose, 0.01 M Na$_3$PO$_4$ pH 7.2 (0.2 ml) i.p. |
| 2 | Solution of Example 6 (0.2 ml) i.p. |
| 3 | Solution of Example 7 (0.2 ml) i.p. |

RESULTS

| Preparation No. | Antibody Response ($\mu$g/ml)-Geometric Average (Standard Error*) | Statistical Significance (Students Test) |
|---|---|---|
| 1 | 4.33 (1.16) | |
| 2 | 7.29 (1.24) | $p < 0.05$ |
| 3 | 7.76 (1.27) | $p < 0.025$ |

*ie. multiplied or divided by same.

EXAMPLE B

PREPARATION OF VACCINE FORMULATION

The purified complexes obtained from Examples 6, 9 and 10 were each dispersed as 1.0 mg per ml of aqueous sterile sodium phosphate (0.01M, pH 7.2). To the resulting solutions, was added 50 mg/ml of lactose with mixing. The solutions were then freeze-dried and stored at $-20°$ C. until used. Reconstitution was achieved after thawing, by solution to the original volume, in sterile, pyrogen-free water.

What is claimed is:

1. A complex comprising a metal constituent and a bacterial capsular polysaccharide constituent, wherein the bacterial capsular polysaccharide constituent contains sialic acid.

2. A complex as claimed in claim 1, wherein the bacterial capsular polysaccharide constituent is colominic acid or capsular polysaccharide specific to serogroup B of *Neisseria meningitidis*.

3. A complex as claimed in claim 1 or claim 2, wherein the said bacterial polysaccharide constituent is complexed with the said metal constituent and also with a further constituent comprising bacterial outer-membrane protein.

4. A complex as claimed in claim 1 or claim 2, wherein the metal constituent comprises aluminum.

5. A complex as claimed in claim 1 or claim 2, wherein the metal constituent comprises a metal which is present in ionic form.

6. A complex as claimed in claim 1 or claim 2, wherein the complex has an apparent molecular weight of at least $2 \times 10^7$.

7. A complex as claimed in claim 1 or claim 2, wherein the metal constituent comprises aluminium and the ratio of sialic acid to aluminium is greater than 1:0.3 w/w.

8. A complex as claimed in claim 1 or claim 2, wherein the metal constituent comprises a metal which is present in ionic form, together with at least one other inorganic ion.

9. A complex as claimed in claim 1 or claim 2, wherein in the metal constituent comprises ruthenium.

10. A vaccine formulation comprising an effective amount of a complex as claimed in claim 1 or claim 2, together with at least 1 adjuvant and a carrier therefor.

11. A vaccine formulation comprising an effective amount of a complex as claimed in claim 1 or claim 2, together with at least one adjuvant or carrier therefor.

12. A method of prophylaxis or treatment of a disease caused by a bacterium having a capsular polysaccharide containing sialic acid in a mannal by administration to said mammal of an effective immunising amount of a complex as claimed in claim 1 or claim 2.

13. A method as claimed in claim 12, wherein the mammal is man.

14. A method as claimed in claim 12 wherein the bacterial disease is cerebrospinal meningitis.

15. A process for preparing a complex which comprises a metal constituent and a bacterial capsular polysaccharide constituent wherein said bacterial capsular polysaccharide constituent contains sialic acid, said process comprising complexing said bacterial capsular polysaccharide which contains sialic acid, and a metal.

16. A process as claimed in claim 15, wherein prior to complexing the bacterial capsular polysaccharide with the metal, the bacterial capsular polysaccharide is in the form of a complex with bacterial outer-membrane protein.

* * * * *